(12) United States Patent
Schneider et al.

(10) Patent No.: US 11,964,601 B2
(45) Date of Patent: Apr. 23, 2024

(54) VEHICLE SEAT HAVING A FLUID CHAMBER UNIT

(71) Applicant: GRAMMER AG, Ursensollen (DE)

(72) Inventors: Florian Schneider, Amberg (DE); Susanne Frohriep, Amberg (DE); Sergej Schustjew, Sulzbach-Rosenberg (DE)

(73) Assignee: GRAMMER AG, Ursensollen (DE)

(*) Notice: Subject to any disclaimer, the term of this patent is extended or adjusted under 35 U.S.C. 154(b) by 365 days.

(21) Appl. No.: 17/467,699

(22) Filed: Sep. 7, 2021

(65) Prior Publication Data
US 2022/0072985 A1 Mar. 10, 2022

(30) Foreign Application Priority Data
Sep. 8, 2020 (DE) .......................... 102020123395.7

(51) Int. Cl.
*B60N 2/90* (2018.01)
*B60N 2/52* (2006.01)

(52) U.S. Cl.
CPC ............. *B60N 2/914* (2018.02); *B60N 2/527* (2013.01)

(58) Field of Classification Search
CPC ................................ B60N 2/914; B60N 2/527
See application file for complete search history.

(56) References Cited

U.S. PATENT DOCUMENTS

| 4,272,117 | A | * | 6/1981 | Vilbeuf | B60N 2/525 296/65.02 |
| 5,477,572 | A | * | 12/1995 | Weingartner | A47C 7/20 297/DIG. 2 |
| 8,651,573 | B2 | * | 2/2014 | Ghisoni | B60N 2/986 297/284.3 |

(Continued)

FOREIGN PATENT DOCUMENTS

| CN | 101602333 | 12/2009 |
| CN | 106364431 | 2/2017 |

(Continued)

OTHER PUBLICATIONS

Extended European Search Report for Europe Patent Application No. 21192408.9, dated Feb. 9, 2022, 9 pages.

(Continued)

*Primary Examiner* — Gertrude Arthur Jeanglaude
(74) *Attorney, Agent, or Firm* — Sheridan Ross P.C.

(57) ABSTRACT

The invention relates to a vehicle seat having an upper seat part for receiving a person, which upper seat part comprises a seat plate part and a seat cushion part, the seat cushion part being arranged above the seat plate part in relation to a height axis of the vehicle seat and the seat plate part and the seat cushion part being arranged so as to at least partially overlap in relation to the height axis, forming an intermediate first overlap region, a fluid chamber unit having at least two fluid chambers being arranged at least partially within the first overlap region between the seat plate part and the seat cushion part, a control unit being provided, designed to (Continued)

introduce and to remove a fluid into/from the at least two fluid chambers so that an expansion in the height axis of the at least two fluid chambers can be controlled.

14 Claims, 7 Drawing Sheets

(56) References Cited

U.S. PATENT DOCUMENTS

| | | | | |
|---|---|---|---|---|
| 8,678,500 | B2* | 3/2014 | Lem | B60N 2/914 |
| | | | | 297/284.6 |
| 8,708,409 | B2* | 4/2014 | Nitsuma | B60N 2/888 |
| | | | | 297/216.12 |
| 10,793,041 | B2* | 10/2020 | Steinberger | B60N 2/914 |
| 2002/0060493 | A1* | 5/2002 | Nishino | B60N 2/70 |
| | | | | 297/452.56 |
| 2008/0100110 | A1 | 5/2008 | Hwang | |
| 2015/0126916 | A1 | 5/2015 | Hall et al. | |
| 2018/0111520 | A1 | 4/2018 | Lem et al. | |
| 2018/0319347 | A1* | 11/2018 | Mozurkewich | B60R 7/043 |

FOREIGN PATENT DOCUMENTS

| | | |
|---|---|---|
| DE | 102004050233 | 11/2006 |
| DE | 102015213995 | 1/2017 |
| DE | 102019101714 | 7/2020 |
| FR | 3086605 | 4/2020 |
| WO | WO 96/41556 | 12/1996 |

OTHER PUBLICATIONS

Article 94(3) Communication for Europe Patent Application No. 21192408.9, dated Jun. 29, 2023, 8 pages.

Official Action with Machine Translation for German Patent Application No. 102020123395.7, dated Mar. 17, 2021, 6 pages.

Official Action (with English translation) for China Patent Application No. 202111050376.X, dated Sep. 28, 2023, 16 pages.

* cited by examiner

VEHICLE SEAT HAVING A FLUID CHAMBER UNIT

CROSS-REFERENCE TO RELATED APPLICATION

This application claims the benefit of German Patent Application No. 10 2020 123 395.7 filed Sep. 8, 2020, the entire contents of which are incorporated herein by reference.

FIELD

The invention relates to a vehicle seat having an upper seat part for receiving a person, which upper seat part comprises a seat plate part and a seat cushion part, the seat cushion part being arranged above the seat plate part in relation to a height axis of the vehicle seat and the seat plate part and the seat cushion part being arranged so as to at least partially overlap in relation to the height axis of the vehicle seat, forming an intermediate first overlap region, in accordance with the preamble of claim 1. The invention further relates to a system having a vehicle seat and to a method for operating the system.

BACKGROUND

In motor vehicles, in particular in commercial vehicles, such as tractors or trucks, it is important to offer the driver the highest possible seating comfort because of the sometimes long journey times. Such vehicle seats are known from the prior art, which make it possible to adjust the seat position of a vehicle driver according to their wishes with regard to ergonomics and driving experience. The corresponding adjustment options, such as the inclination of the seat height, the position and orientation of individual components of the seat, such as the backrest, headrest, seat cushion part, or even adjustment of a suspension and/or damping device are in this context usually adjusted consecutively before the start of the journey and are no longer or hardly changed during a journey.

A driver who is in the same sitting position, in particular on long journeys—without movement—, can experience pain from overstressing parts of the body, in particular the muscles and intervertebral discs, due to a monotonous and one-sided sitting posture. Furthermore, static discomfort can occur. In addition to the physical or health impairments, long journeys can result in symptoms of fatigue, which in turn can result in a reduction in attention and reaction time, which significantly increases the risk of accidents, especially on long journeys without breaks.

SUMMARY

It is therefore the object of the invention to provide a vehicle seat which eliminates the aforementioned disadvantages of the prior art and prevents physical impairments and symptoms of fatigue, in particular during long driving times.

This object is achieved by a vehicle seat having an upper seat part for receiving a person, which upper seat part comprises a seat plate part and a seat cushion part, the seat cushion part, in relation to a height axis of the vehicle seat which is arranged above the seat plate part and the seat plate part and the seat cushion part being arranged so as to at least partially overlap in relation to the height axis of the vehicle seat, forming an intermediate first overlap region, a fluid chamber unit having at least two fluid chambers being arranged at least partially within the first overlap region between the seat plate part and the seat cushion part, a control unit being provided, designed to introduce and to remove a fluid into/from the at least two fluid chambers so that an expansion in the height axis of the at least two fluid chambers can be controlled.

According to the invention, an upper seat part is understood to mean that part of a vehicle seat on which a person, preferably the driver of the vehicle, is seated. The upper seat part in this case comprises the seat plate part and the seat cushion part, a person preferably resting on the seat cushion part. The seat cushion part is preferably made of a flexible, reversibly deformable material, preferably a rigid foam. The seat cushion part is preferably connected to an upper side of the seat plate part by means of a force-fit, form-fit or material-fit connection. The seat plate part is furthermore preferably arranged to be connected to a seat base part, it being possible for the seat base part to be connected to a body of the vehicle by means of a force-fit, form-fit, or material-fit connection, or it being possible for the seat base part to be connected to the vehicle body via a known suspension and/or damping device. The vehicle seat according to the invention preferably also has a backrest part, which is preferably connected to the seat base part and comprises a back plate part and a back cushion part. The vehicle seat according to the invention is preferably arranged in a motor vehicle, particularly preferably in a commercial vehicle, such as a commercial vehicle for transporting people (e.g., a bus), a commercial vehicle for transporting loads (e.g., trucks) or other commercial vehicles.

The vehicle seat extends along a height axis, a width axis, and a length axis, the respective axes being assigned to two directions in each case. The height axis thus comprises the directions towards the top and towards the bottom. The width axis comprises the directions towards the right and towards the left. The length axis comprises the directions towards the front and towards the rear.

By means of the fluid chamber unit according to the invention having at least two fluid chambers, which fluid chamber unit can be filled with a fluid in a controllable manner by means of a control unit, and the fluid can also be removed again, micro-movements in the seat cushion part can be generated by power transmission from the fluid chamber unit to the seat cushion part, which mobilise a person who is sitting on the vehicle seat, since the micro-movements are transmitted from the seat cushion part to the person. This results in a reversible deformation of the seat cushion part. The micro-movements can in this case promote the elasticity of the intervertebral discs, in particular on long journeys, and thus prevent intervertebral disc defects, reduce or prevent static discomfort, avoid long periods of static muscle tension and reduce muscle fatigue, and improve the attention and reaction time of the person sitting in the vehicle seat.

The control unit is in this case arranged in or on the vehicle seat or is located at any position within the vehicle in which the vehicle seat is arranged. It is also conceivable that the control unit according to the invention is an existing control unit of the vehicle able to undertake the tasks, for example by means of suitable software.

The fluid is preferably a gas or a liquid. The gas is preferably air. The liquid is further preferably water. It is conceivable in this case that the material and configuration of the fluid chamber unit is adapted to the fluid used. According to the invention, introduction of the fluid into the fluid chamber unit or the at least two fluid chambers is understood to mean active introduction, which in turn means introduction under pressure (e.g., compressed air). This is possible, for example, in the case of known pumps (liquid) or compressors (gas). Removing the fluid can be understood to mean either active removal or passive removal. In the case of active removal, the fluid is removed, for example, by applying a negative pressure. Passive removal can be initiated, for example, via the weight of a person sitting on the seat cushion part, the control unit preferably opening a suitably arranged valve in a controlled manner for this purpose, via which valve the fluid can flow or be removed since the weight of the person sitting on the vehicle seat exerts a pressure due to the weight on the fluid chamber unit or the at least two fluid chambers. An amount of fluid to be removed and a removal rate (fluid delivery rate) can preferably be adjusted by means of the control unit, for example via the opening duration and width of a valve.

According to a preferred embodiment, the at least two fluid chambers are each designed to receive the fluid. A fluid delivery device is preferably provided, which is connected to the control unit at least for signalling purposes, which fluid delivery device is at least fluidically connected, independently, to each of the at least two fluid chambers, and is designed to transport the fluid into and/or from each of the at least two fluid chambers, it being possible for the fluid to be introduced individually into each of the at least two fluid chambers and to be removed individually from each of the at least two fluid chambers. The fluid delivery device is preferably a pump or a compressor. The fluid delivery device is preferably arranged in or on the vehicle seat, it also being conceivable that the fluid delivery device is arranged adjacently to the vehicle seat or somewhere in the vehicle in which the vehicle seat is located. By means of the fluid delivery device, which is connected to the at least two fluid chambers of the fluid chamber unit, the fluid can be introduced and/or removed individually into/from the at least two fluid chambers in a controllable manner by means of the control unit.

According to one conceivable embodiment, the at least two fluid chambers can each be transferred independently of one another from a first state into at least one second state by introducing at least one first defined amount of fluid and can each be transferred independently of one another from the at least one second state into the first state by removing the at least one first defined amount of fluid, the at least two fluid chambers having a first expansion in the height axis of the vehicle seat in the first state and at least a second expansion in the height axis of the vehicle seat in the at least one second state, the first and the at least one second expansion differing in the height axis. A large number of second states are possible, depending on the amount of fluid introduced or removed. Accordingly, it is conceivable that the first state represents a state in which no or substantially no fluid is introduced into the at least two fluid chambers. The first expansion in the height axis of the first state is preferably the minimum possible expansion in the height axis of the at least two fluid chambers. The first state can therefore also be referred to as the basic state, the non-active state, or the off state of the at least two fluid chambers or the fluid chamber unit. The expansion in the height axis of the fluid chamber unit or the at least two fluid chambers takes place towards the top in the direction of the seat cushion part since the seat cushion part arranged above is designed to be deformable/flexible, whereas the seat plate part is designed to be rigid. In this way, the expansion of the fluid chamber unit or the at least two fluid chambers in the height axis can be adjusted or varied in a controlled manner by the introduction/removal of the fluid, whereby the micro-movements are generated that are transmitted to the seat cushion part and from there to a person who sits on the vehicle seat or on the seat cushion part.

Preferably, fluid can be introduced into each provided fluid chamber of the fluid chamber unit individually and independently of other fluid chambers of the fluid chamber unit, and fluid can be removed from each provided fluid chamber of the fluid chamber unit individually and independently of other fluid chambers of the fluid chamber unit. The control unit and the fluid delivery unit are in this case designed to introduce and to remove the fluid individually and independently with a variable amount of fluid into/from each fluid chamber of the fluid chamber unit, to introduce and remove the fluid at a variable speed or over a variable period of time (variable fluid delivery rate), and/or to introduce or remove the fluid at a variable point in time. A so-called movement pattern can thus be made possible via the different controllability of the at least two fluid chambers.

The fluid delivery device is preferably fluidically connected to each of the at least two fluid chambers individually by at least one fluid connection element. The fluid connection element is preferably a hose or the like which is suitable for transporting the corresponding fluid. By means of the fluid delivery device, which is individually connected to each of the at least two fluid chambers of the fluid chamber unit, the fluid can be introduced and/or removed individually into/from the at least two fluid chambers in a controllable manner by means of the control unit. By providing a plurality of fluid chambers for the fluid chamber unit, which can be filled with the fluid separately by means of the individual fluidic connection to the fluid delivery device, and the fluid can be removed, alternating micro-movements can be generated in the seat cushion part and, for example, different movement programs can be defined. By arranging a plurality of individual fluid chambers into which fluid can be introduced and removed separately by means of the control unit, the expansion of the fluid chamber unit in the height axis can be adjusted or controlled, depending on the region, or in portions (left/right and/or front/rear). For example, the fluid can thus be introduced into both fluid chambers at the same time into the at least two fluid chambers; the fluid can be removed from both fluid chambers at the same time; the fluid can be removed from one fluid chamber and introduced into the other fluid chamber at the same time; or the fluid can only be removed or introduced from one of the fluid chambers.

According to a preferred embodiment, the at least two fluid chambers are arranged adjacently in relation to a width axis or a length axis of the vehicle seat. The at least two fluid chambers of the fluid chamber unit are preferably arranged adjacently in a plane along the length axis and the width axis or perpendicular to the height axis. Thus, the at least two fluid chambers are either preferably arranged in succession (front/rear) along the length axis or side by side (left/right) along the width axis. The area in which the expansion in the height axis can be adjusted can thus be increased.

The fluid chamber unit particularly preferably has four fluid chambers (first, second, third, fourth fluid chambers) which are each connected to the fluid delivery device independently of one another. The four fluid chambers are arranged in the plane along the length axis and the width axis (perpendicular to the height axis). Further preferably, the four fluid chambers are arranged side by side, bilaterally adjacent. Preferably, a first fluid chamber, when viewed along the length axis towards the front and to the right of a second fluid chamber, or the first fluid chamber and the second fluid chamber are in this case arranged side by side along the width axis; a third fluid chamber, when viewed along the length axis towards the front and to the right of a fourth fluid chamber, or the third fluid chamber and the fourth fluid chamber are arranged side by side along the width axis. The first fluid chamber and the second fluid chamber are arranged behind the third fluid chamber and the fourth fluid chamber in relation to the length axis, the first and third and the second and fourth fluid chambers being arranged in succession.

A maximum second expansion of the at least two fluid chambers is preferably the same in the height axis, it also being conceivable that this expansion would be different. The at least two fluid chambers thus preferably each have a second expansion in the height axis of up to 100 mm, preferably up to 75 mm, more preferably up to 50 mm, and particularly preferably 40 mm. The second expansion of the fluid chambers in the height axis can also be referred to as the chamber stroke. Preferably, the shape of each of the fluid chambers and thus the shape of the fluid chamber unit is arbitrary and can be adapted to the available installation space.

According to a preferred embodiment, the control unit is connected to the fluid delivery device, at least for signalling purposes, and is designed to control the fluid delivery device by means of a pulse-width-modulated control signal. The control unit is preferably connected power-electronically to the fluid delivery device. A power electronic connection is understood to mean a connection by means of which power is also transmitted to the signal or with the signal. The control unit is thus designed to transmit a pulse-width-modulated control signal to the fluid delivery device. In this way, the power of the fluid delivery device and the associated amount of fluid which is to be introduced into the fluid chambers can advantageously be adjusted or controlled by means of the control unit. The control unit is preferably designed to control or activate the fluid delivery unit, in particular by means of the pulse-width-modulated control signal, in such a way that at least one amount of fluid, an introduction/removal fluid rate and/or a fluid delivery time (or step length) for the fluid, which fluid can be introduced/removed into/from the at least two fluid chambers of the fluid chamber unit, can be adjusted or controlled. Particularly preferably, this applies individually to each of the provided fluid chambers of the fluid chamber unit. Thus, the introduction and removal of the fluid into each of the provided fluid chambers of the fluid chamber unit can preferably be controlled or adjusted separately by means of the control unit. Particularly preferably, an amount of fluid to be introduced/removed into/from the fluid chamber, the fluid delivery rate and the time of introduction/removal of the fluid for each fluid chamber of the fluid chamber unit can be controlled or adjusted independently of one another by means of the control unit.

A pulse-width-modulated control signal is preferably understood to be a signal which is transmitted from the control unit to the fluid delivery device connected thereto at least for signalling purposes, preferably power-electronically, and which is designed to control the fluid delivery device, it being possible for a power generated by means of the fluid delivery device to be adjusted or controlled via the pulse-width-modulated control signal. Pulse-width modulation (PWM) is a type of modulation in which a voltage, a current or the like changes between two fixed values at a fixed frequency. The information to be transmitted is stored in the duty ratio/duty cycle. A pulse-width modulation period consists of the pulse and the pause. The degree of modulation is expressed in percent in the duty cycle of the pulse length to the period duration (pulse+pause). The generation and use of pulse-width-modulated signals is sufficiently known from the prior art, which is why it will not be discussed in more detail herein.

According to a preferred embodiment, the fluid chamber unit is designed to be substantially plate-like. A cover element is preferably arranged below the fluid chamber unit and between the seat plate part and the fluid chamber unit in relation to the height axis of the vehicle seat. A plate element is further preferably arranged above the fluid chamber unit and between the seat cushion part and the fluid chamber unit in relation to the height axis of the vehicle seat. The fluid chamber unit is further preferably arranged between the cover element and the plate element in relation to the height axis. The cover element and the plate element preferably serve to mechanically protect the fluid chamber unit or the fluid chambers from damage. Furthermore, the fluid chamber unit can preferably be fastened to the seat plate part by means of the cover element. The plate element also preferably ensures that the punctual movements (second expansions in the height axis) of the fluid chamber unit or the fluid chambers are transmitted in a planar manner to the seat cushion part, i.e., a planar power transmission takes place. Thus, the introduction of the fluid into at least one fluid chamber of the fluid chamber unit results in the deflection of the plate element in the height axis, which is reversible by removing the fluid.

According to a preferred embodiment, the cover element and the plate element are arranged so as to at least partially overlap in relation to the height axis of the vehicle seat, forming an intermediate second overlap region. The fluid chamber unit is preferably at least partially, preferably completely, arranged within the second overlap region between the cover element and the plate element. The cover element and the plate element are further preferably arranged at least partially, preferably completely, within the first overlap region between the seat plate part and the seat cushion part. The formation of the second overlap region between the cover element and the plate element in the height axis and the arrangement of the fluid chamber unit in the second overlap region can ensure mechanical protection, fastening and planar power transmission.

According to a preferred embodiment, the cover element makes contact with the seat plate part on the upper side. The plate element preferably makes contact with the seat cushion part on the underside. Particularly preferably, the plate element is arranged free of connections with respect to the fluid chamber unit and the seat cushion part and is arranged only in contact with the fluid chamber unit and the seat cushion part, so that the power transmission can take place particularly advantageously by means of the expansion of the fluid chamber unit or the fluid chambers in the height axis and is not impaired by fixed connections. Further preferably, the cover element and the plate element each have an expansion in the height axis of the vehicle seat in a range from 0.1 mm to 10 mm, preferably in a range from 0.5 mm to 8 mm, more preferably in a range from 1 mm to 6 mm, particularly preferably in a range from 1.5 mm to 4 mm, and particularly preferably of 2 mm. As a result of this preferred expansion in the height axis, also referred to as thickness, the space requirement in the height axis is kept low, since there is no large installation space available in this case. Preferably, an expansion of the cover element and the plate element perpendicular to the height axis of the vehicle seat is greater than an expansion of the fluid chamber unit perpendicular to the height axis of the vehicle seat in order to simplify an arrangement of the fluid chamber unit in the second overlap region. The fluid chamber element, the cover element, and the plate element are preferably designed to be plate-like in order to ensure a small space requirement in the height axis.

According to a preferred embodiment, the cover element is mechanically connected to the fluid chamber unit. Further preferably, the cover element consists of a flexible material, preferably a textile material, more preferably a felt. The fluid chamber unit is preferably connected to the cover element by connecting means such as rivets, bolts, clips, or the like. In this way, the cover element can ensure that the fluid chamber unit is fastened in a fixed position with respect to the seat cushion part. According to a preferred embodiment, the plate element is designed to be planar. The plate element preferably consists of a flexible material, preferably a plastics material. The flexible configuration and flexibility thus allow an adaptation and optimal power transmission from the fluid chamber unit to the seat cushion part. Further preferably, the plate element is designed from a suitable polymeric plastics material, for which purpose, for example, polyethylene, polypropylene, polyvinyl chloride, polyurethane, polyethylene terephthalate, or the like can be used, the selection not being restricted to these plastics materials. Preferably, any flexible material is suitable which is deformable or bendable in the height axis by the movements of the fluid chamber unit or the fluid chambers in order to transmit the movements to the seat cushion part.

The object of the invention is also achieved by a system, preferably arranged in a vehicle, comprising a vehicle seat according to any of claims 1 to 6 and an activation unit which is connected at least for signalling purposes to the control unit and which is designed to transmit an activation signal to the control unit to initiate an introduction and/or removal of a fluid into/from at least one fluid chamber of at least two fluid chambers of a fluid chamber unit.

An activation unit is understood to mean a device by means of which an activation signal can be transmitted to the control unit, the control unit outputting a pulse-width-modulated control signal to the fluid delivery device in response to the activation signal and the fluid delivery device introducing and/or removing the corresponding defined amount of fluid into/from the at least two fluid chambers of the fluid chamber unit.

According to a preferred embodiment, the activation unit comprises a manually actuatable operating unit and/or a body function recognition unit. The body function recognition unit is preferably designed to detect at least one body function of a person sitting on the vehicle seat, and has at least one first sensor. The manually actuatable operating unit can preferably be actuated by a person sitting on the vehicle seat, as a result of which the activation signal is transmitted to the control unit. The operating unit can therefore also be referred to as an on/off switch unit. In this way, the person in the vehicle seat can use the operating unit to determine when and whether the fluid chamber unit should be active, depending on requirements. Further preferably, an amount of fluid that is introduced into the fluid chambers can be adjusted by means of the operating unit (this corresponds to an intensity). Likewise, a fluid delivery rate can preferably be adjusted by means of the operating unit, this corresponding to an amount of fluid per time. This applies to both the introduction and removal of the fluid. The operating unit is preferably arranged in such a way that it can be easily reached and operated by the person who is also sitting in the vehicle seat. Thus, the operating unit is preferably arranged in/on a dashboard region, in/on a steering wheel, in/on an armrest, or in/on a centre console of a vehicle in which the vehicle seat is arranged.

The body function recognition unit can preferably detect at least one heart rate, a pulse, a breathing rate, a blink rate of the eyelids, a pupil size, a body temperature, or the like by means of at least one first sensor. The first sensor is preferably an optical, electrical, magnetic, electromagnetic, thermal, capacitive, acoustic, or mechanical sensor. The first sensor is further preferably arranged in or on any component of the vehicle seat, for example in the seat cushion part or the backrest part. By means of the detected sensor data, the body function recognition device can preferably infer a body function, which in turn allows conclusions to be drawn about a (health) state of the person sitting on the vehicle seat. The body function recognition unit preferably automatically initiates the transmission of the activation signal to the control unit if a (health) condition such as tiredness, lack of concentration, muscle tension or the like is recognised, which could impair driving the vehicle. Particularly preferably, the body function recognition device automatically transmits an activation signal to the control unit when sensor data are detected by means of the at least one first sensor which indicate a predetermined body function. For example, based on a specific heart rate, blinking frequency or a pulse, conclusions can be drawn about a specific body function, e.g. tiredness. The body function recognition device is preferably designed to determine at least one body function of a person sitting on the vehicle seat based on detected sensor data from at least one first sensor.

According to a preferred embodiment, the control unit comprises a storage unit connected thereto, at least for signalling purposes. At least one movement program is preferably stored on the storage unit, a movement program advantageously being a predetermined sequence or a predetermined process of introducing and removing fluid into at least one fluid chamber of the fluid chamber unit. The movement programs can be predetermined and stored unchangeably on the storage unit or can be changed and/or created and stored by a person. The respectively defined amounts of fluid for introduction/removal into/from the at least two fluid chambers are preferably stored on the storage unit and can be called up by means of the control unit. Further preferably, a fluid delivery rate for introducing/removing the fluid for each of the at least two fluid chambers is also stored in the storage unit. Particularly preferably, points in time or a sequence for introducing/removing the fluid into/from the at least two fluid chambers are also stored.

The object of the invention is further achieved by a method for operating a system according to either claim 7 or claim 8, comprising the steps of:
  a) receiving an activation signal from an activation unit by means of a control unit;
  b) outputting a pulse-width-modulated control signal to a fluid delivery unit by means of the control unit;
  c) introducing a fluid into at least one fluid chamber of at least two fluid chambers of a fluid chamber unit.

According to a preferred embodiment, the method comprises a further step:
  d) removing the fluid from the at least one fluid chamber of the fluid chamber unit.

According to a preferred embodiment, steps c) and d) of the method can be repeated as often as desired. In this way, movement patterns can result which can be stored as movement programs on a storage unit of the control unit. In step c), the fluid can preferably be introduced into a plurality of fluid chambers at the same time. Further preferably, in step d), the fluid can be removed from a plurality of fluid chambers at the same time. For different fluid chambers—i.e., at least two fluid chambers must be provided—steps c) and d) can preferably take place simultaneously; fluid being removed from one fluid chamber into which fluid has previously been introduced, and fluid being introduced into another fluid chamber into which no fluid has yet been introduced or the fluid has already been removed.

In step c), different amounts of fluid can preferably be introduced into a plurality of (at least two) fluid chambers. Likewise preferably, in step d), different amounts of fluid can be removed from a plurality of (at least two).

Furthermore, the object is achieved by a vehicle, in particular a motor vehicle, comprising the system according to any of claim 11 or 12.

In the following, a preferred embodiment of the vehicle seat according to the invention, the system and the method are shown by way of example, although the invention is not intended to be restricted to this example.

A vehicle seat according to the invention is provided, the fluid chamber unit having four separate fluid chambers which are each individually fluidically connected to a compressed air-conveying pump (fluid delivery device). The fluid chambers can therefore also be referred to as air chambers in this example. Accordingly, the fluid chambers are designed to be substantially rectangular, in particular square. The four fluid chambers are in this case arranged adjacently in the plane of the length axis and the width axis (perpendicular to the height axis), the four fluid chambers being arranged so that in turn a rectangular, in particular square shape of the fluid chamber unit results.

The arrangement of the four fluid chambers of the fluid chamber unit is shown schematically as follows (as viewed along the height axis from the top towards the bottom):

| Fluid chamber 1 | Fluid chamber 2 |
|---|---|
| Fluid chamber 3 | Fluid chamber 4 |

When the control unit receives an activation signal from the activation unit, the control unit outputs at least one pulse-width-modulated control signal to the pump, whereupon a predetermined movement program is executed. The predetermined movement program (table 1), consisting of 4 sequences, can be switched on/off, for example, by a manually operated operating unit and the intensity (via the amount of fluid introduced into the fluid chambers) via the pulse width modelling (PWM) of the pump by means of the control signal of the control unit can be changed in three stages (Table 2/3). The pumping time or fluid delivery time (step length) is 5 seconds when using a pump with a characteristic Pmax of 800 hPa and a filling time (given by the fluid delivery rate) of ≤8 s (1 l @ 550 hPa).

TABLE 1 predetermined movement program

| | Sequence | Duration [min] |
|---|---|---|
| 1 | Left-right change | 15 |
| 2 | Pause | 5 |
| 3 | Cross | 15 |

TABLE 1-continued predetermined movement program

| | Sequence | Duration [min] |
|---|---|---|
| 4 | Pause | 25 |
| 5 | Repeating sequences 1-4 | 60 |

The movement pattern shown in Table 1 comprises five sequences. The sequence "pause" (sequences 2 and 4) refer to the state when all four fluid chambers have a minimal expansion in the height axis (so-called basic state, in which substantially no fluid has been introduced or all fluid has been removed), when substantially all fluid has been removed from the fluid chambers.

The sequence 1 "right-left change" refers to a sequence of introduction and removal steps of the fluid (analogous to steps c) and d) of the method according to the invention) in accordance with:

Step 1: Introducing the fluid into the fluid chamber 1 and into the fluid chamber 3;

Step 2: Removing the fluid from the fluid chamber 1 and from the fluid chamber 3 and introducing the fluid into the fluid chamber 2 and into the fluid chamber 4;

Step 3: Introducing the fluid into the fluid chamber 1 and into the fluid chamber 3 and removing the fluid from the fluid chamber 2 and from the fluid chamber 4.

The sequence 3 "cross" refers to a sequence of introduction and removal steps of the fluid (analogous to steps c) and d) of the method according to the invention) in accordance with:

Step 1: Introducing the fluid into the fluid chamber 1;

Step 2: Removing the fluid from the fluid chamber 1 and introducing the fluid into the fluid chamber 4;

Step 3: Removing the fluid from the fluid chamber 1 and from the fluid chamber 4 and introducing the fluid into the fluid chamber 2;

Step 4: Removing the fluid from the fluid chamber 1, from the fluid chamber 4 and from the fluid chamber 2 and introducing the fluid into the fluid chamber 3;

Step 5: Removing the fluid from the fluid chamber 4, from the fluid chamber 2 and from the fluid chamber 3 and introducing the fluid into the fluid chamber 1.

After the sequences 1 and 3, the fluid is removed from each fluid chamber, so that each fluid chamber is in the first state. Steps 3 and 4 of sequence 1 and steps 2 to 5 of sequence 3 can preferably be repeated as desired. The fluid chamber unit is inflated or emptied alternately "left and right" by means of sequence 1, and a fluid chamber of the fluid chamber unit is always inflated by means of sequence 3, the fluid being introduced in steps 2 and 4 in each case in the diagonally arranged ("crossed") fluid chamber.

As already mentioned above, the intensity can be adjusted by means of the amount of fluid that is introduced into each fluid chamber, as well as the pumping time (fluid delivery rate or step length). The intensity or amount of fluid is preferably controlled or adjusted by the control unit by means of the pulse-width-modulated control signal. The intensity of sequence 1 (Table 2) and sequence 3 (Table 3) can be set in three stages as follows:

TABLE 2

| Sequence parameters of sequence 1 | | | |
| --- | --- | --- | --- |
| Intensity | 1 | 2 | 3 |
| Step length [s] | 5 | 5 | 5 |
| PWM control signal [%] | 70 | 85 | 100 |

TABLE 3

| Sequence parameters of sequence 3 | | | |
| --- | --- | --- | --- |
| Intensity | 1 | 2 | 3 |
| Step length [s] | 5 | 5 | 5 |
| PWM control signal [%] | 60 | 85 | 100 |

The example above shows the possibility that the fluid chamber unit offers by filling and emptying a plurality of fluid chambers independently of one another with fluid, whereby movement patterns can be generated that address differently the muscles involved and, thanks to the variety, keep attention high.

The embodiments relating to the vehicle seat according to the invention should apply mutatis mutandis to the system, the method, and the vehicle according to the invention, and vice versa.

BRIEF DESCRIPTION OF THE DRAWINGS

Further advantages, objectives, and characteristics of the present invention are illustrated by way of the accompanying drawings and the following descriptions, which show and describe a control apparatus by way of example.

In the drawings.

DETAILED DESCRIPTION

Figure 1:
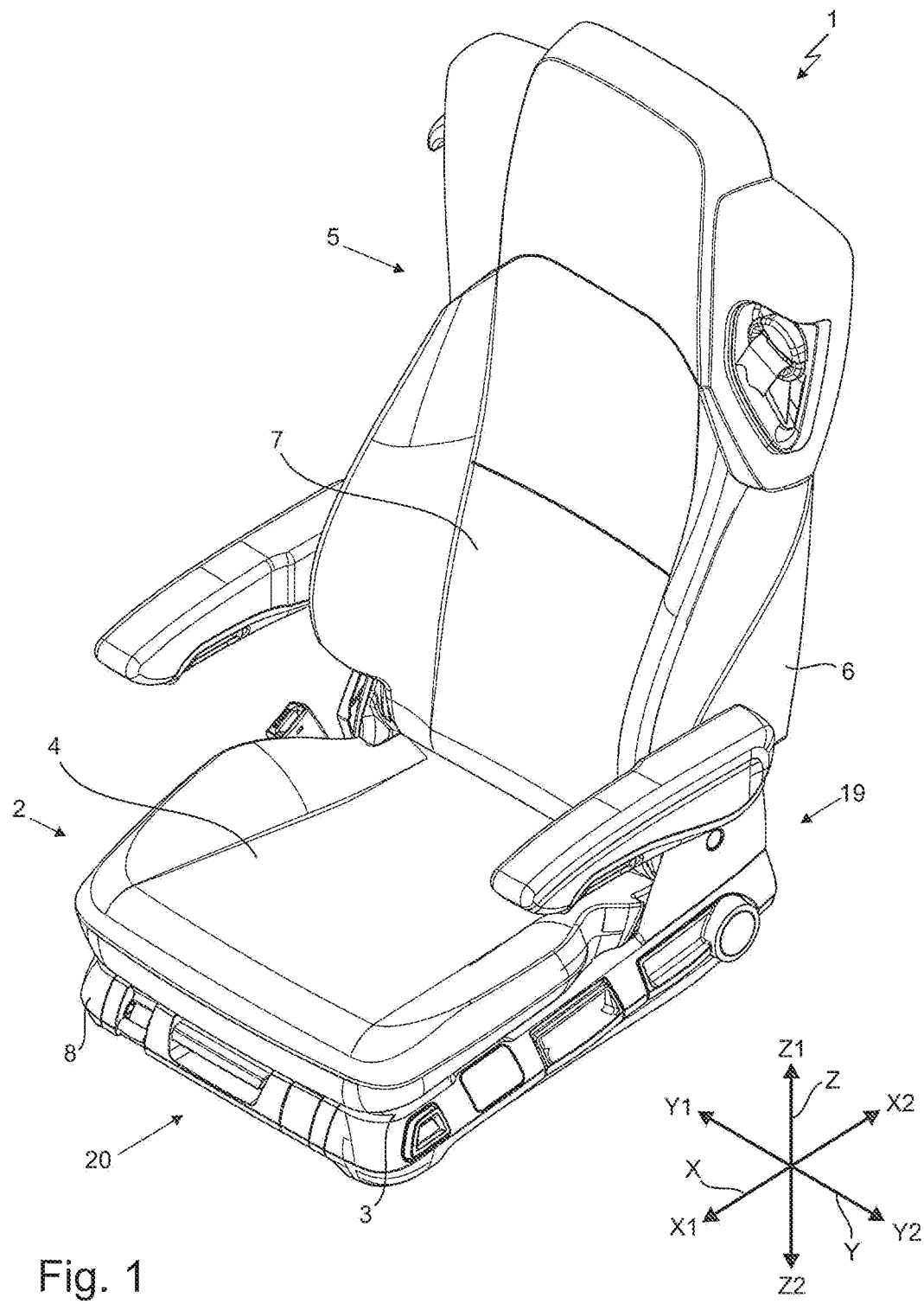
FIG. 1 shows a vehicle seat according to a preferred embodiment of the invention.

FIG. 1 shows a vehicle seat 1 according to a preferred embodiment of the invention. The vehicle seat 1 is preferably arranged in a motor vehicle (not shown), particularly preferably in a commercial vehicle. In FIGS. 1 to 5, no control unit and no fluid delivery device are shown in each case. The arrangement of these components in or on the vehicle seat 1 or in the vehicle.

The vehicle seat 1 extends along a height axis Z, a width axis Y, and a length axis X, the respective axes being assigned to two directions in each case. The height axis Z thus comprises the directions towards the top Z1 and towards the bottom Z2. The width axis Y comprises the directions towards the right Y1 and towards the left Y2. The length axis X comprises the directions towards the front X1 and towards the rear X2.

The vehicle seat 1 according to FIG. 1 has an upper seat part 2, comprising a seat plate part 3 and a seat cushion part 4, and a backrest part 5, comprising a back plate part 6 and a back cushion part 7. The upper seat part 2 and the backrest part 5 are at least mechanically connected to one another, the upper seat part 2 and the backrest part 5 preferably being movable relative to one another. The seat upper part 5 is arranged at least mechanically with a seat base part 8, the upper seat part 2 being arranged above the seat base part 8 in relation to the height axis Z. The seat base part 8 can either be arranged directly on a vehicle body (not shown) or fastened thereto via a damping and/or suspension device (not shown). The seat cushion part 4 is arranged above the seat plate part 3 in relation to the height axis Z of the vehicle seat 1, the seat cushion part 4 being fastened to the seat plate part 3.

Figure 2A:
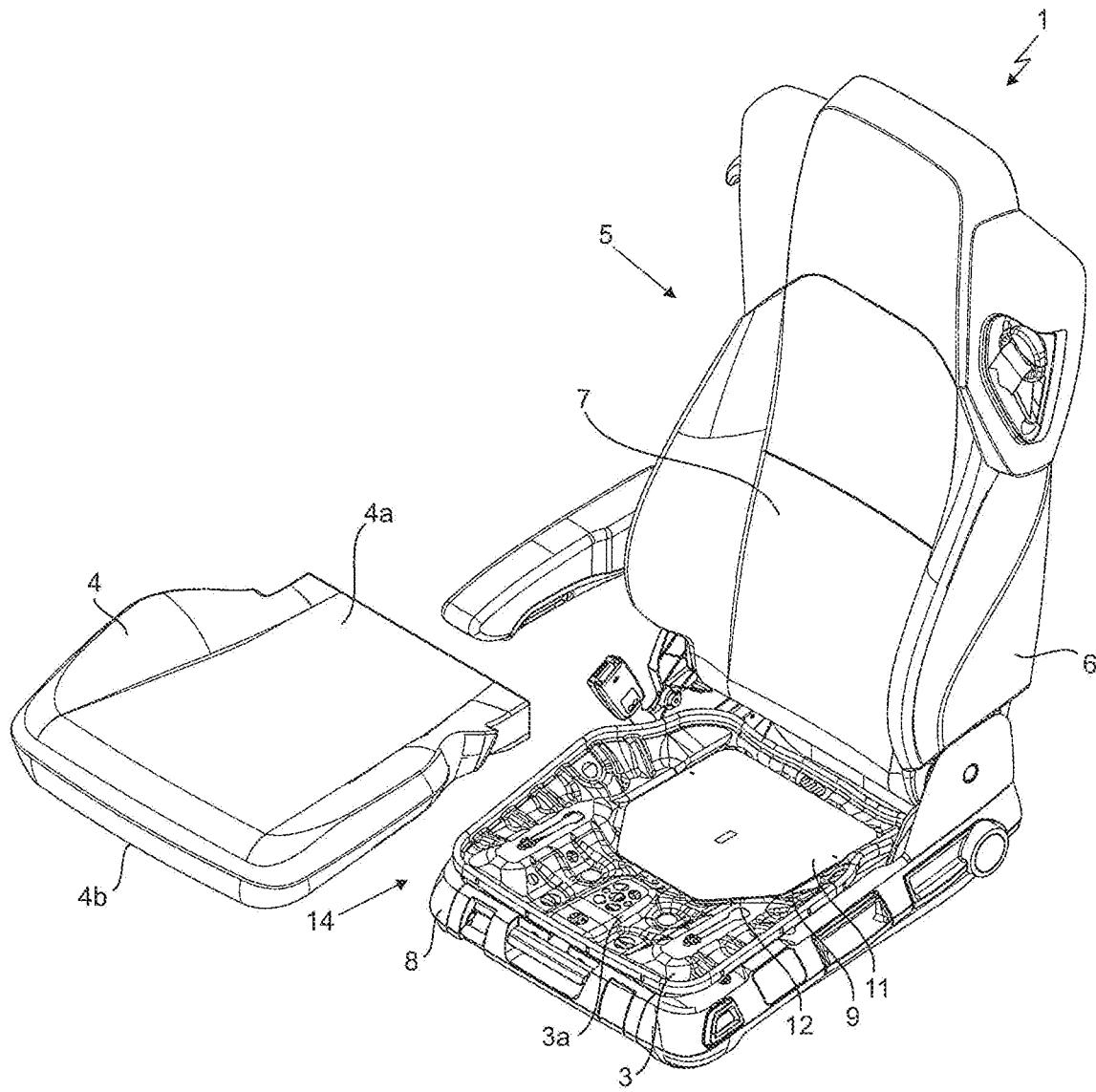
FIG. 2a, 2b are various exploded views of the vehicle seat according to FIG. 1.
Figure 2B:
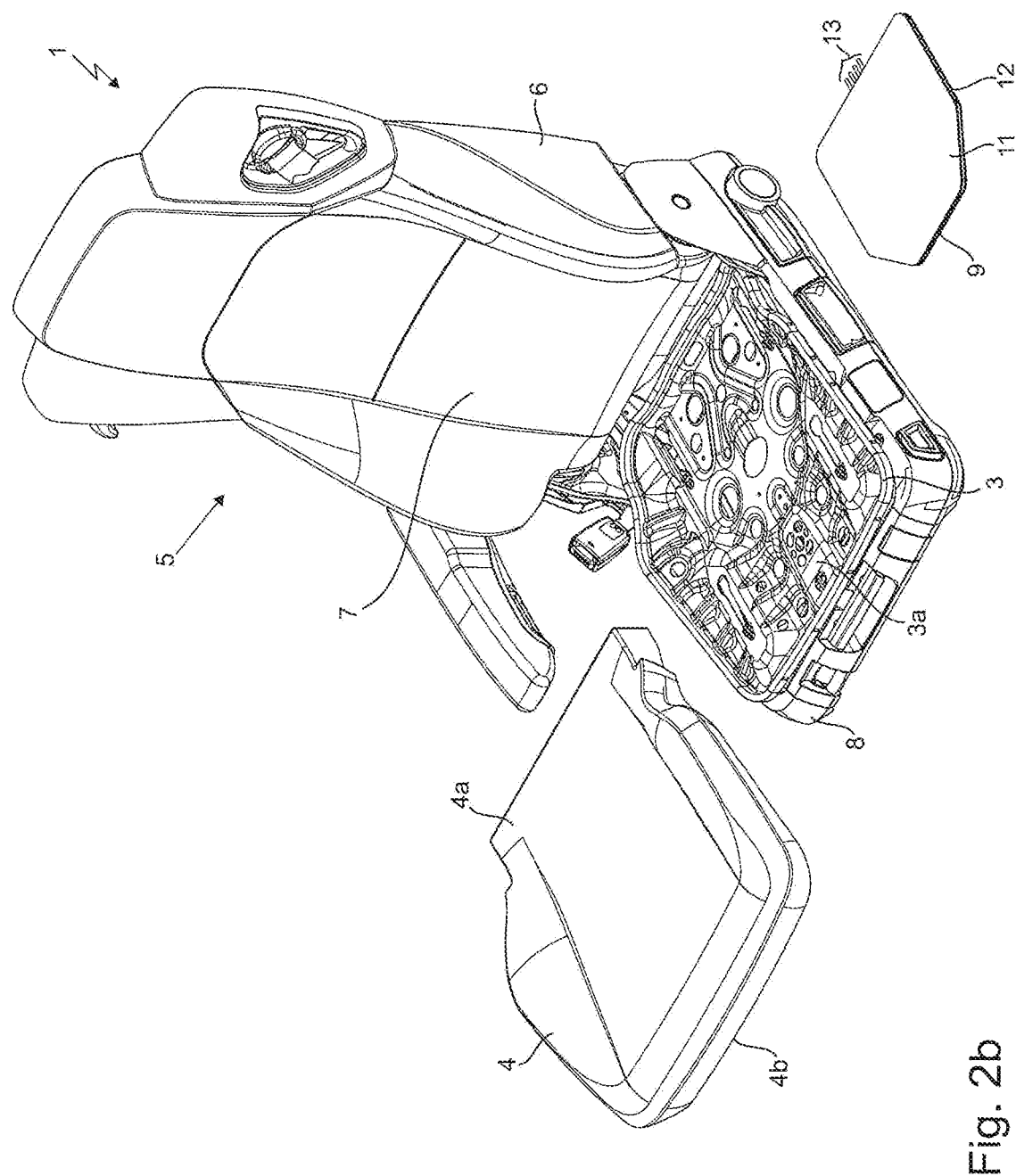

FIG. 2 shows the vehicle seat 1 according to FIG. 1 in an exploded view, relating to the seat cushion part 4. The seat cushion part 4 has an upper side 4a and an underside 4b. In an assembled state, the seat cushion part 4 is fastened to an upper side 3a of the seat plate part 3 via the underside 4b. According to the embodiment shown, the seat plate part 3 and the seat cushion part 4 are arranged substantially congruently in relation to the height axis Z and form an intermediate first overlap region 14. The first overlap region 14 is arranged between the seat plate part 3 and the seat cushion part 4 in relation to the height axis Z and is delimited along the height axis Z towards the top Z1 by the underside 4b of the seat cushion part 4 and towards the top Z2 by the upper side 3a of the seat plate part 3.

Furthermore, a fluid chamber unit 9 is arranged together with a plate element 11 and a cover element 12 in the first overlap region 14 between the seat cushion part 4 and the seat plate part 3. The fluid chamber unit 9, the plate element 11, and the cover element 12 are arranged completely within the first overlap region 14. The plate element 11 is arranged to be in contact with the underside 4b of the seat cushion part, and the cover element 12 is arranged to be in contact the upper side 3a of the seat plate part 3. The fluid chamber unit 9 is arranged between the plate element 11 and the cover element 12 in relation to the height axis Z. A more detailed description of the fluid chamber unit 9, the plate element 11, and the cover element 12 and the arrangement thereof is given in FIGS. 4 to 6.

The fluid chamber unit 9, the plate element 11, and the cover element 12 are arranged in relation to a length axis X in a rear portion 19 of the upper seat part 2 or the seat plate part 3 and the seat cushion part 4, the rear portion 19 being arranged in relation to the length axis X in a front portion 20 of the upper seat part 2, or the seat plate part 3 and the seat cushion part 4. This arrangement is preferred because a buttock and/or lower back region of a person who is sitting on the vehicle seat 1 or the upper seat part 2 or the seat cushion part 4 is substantially located in the rear portion 19, the thighs of the person being arranged substantially in the front portion 20. Thus, intervertebral disc elasticity and muscle tension in the buttock region can be promoted or reduced particularly effectively.

Figure 3:
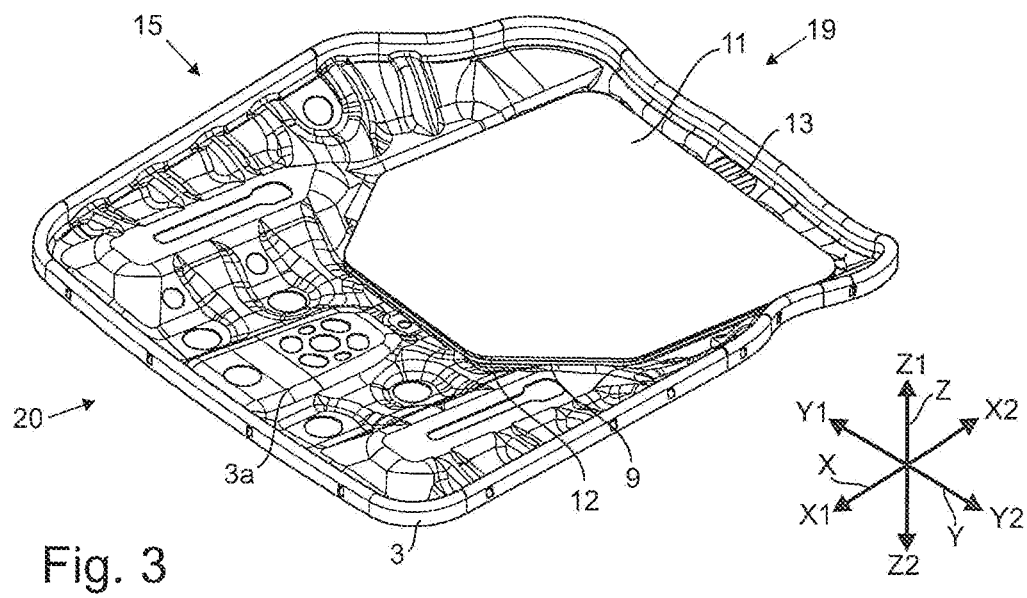
FIG. 3 is a detailed view of a seat plate part having a fluid chamber unit according to FIG. 1.

FIG. 3 shows a further exploded view, relating to the seat cushion part 4, the fluid chamber unit 9, the plate element 11, and the cover element 12 of the vehicle seat 1 according to FIG. 1. In FIG. 3, four fluid connection elements 13 can also be seen, which are at least fluidically connected to the fluid chamber unit 9 or fluid chambers of the fluid chamber unit 9. A more detailed explanation is given in FIGS. 4 to 6.

FIG. 4 is a detailed view of the seat plate part 3 having the fluid chamber unit 9, the plate element 11, and the cover element 12 according to the embodiment shown in FIG. 1 in an installed state.

According to the embodiment shown, the seat plate part 3 is designed as a seat shell part, the seat shell part enclosing a region 15 open towards the top Z1 on the upper side 3a. The seat cushion part 4 is thus arranged at least partially within this enclosed region 15. The fluid chamber unit 9, the plate element 11, and the cover element 12 are arranged completely within this enclosed region 15. Furthermore, the first overlap region 14 is also arranged completely in this enclosed region 15, designed by the seat plate part 3 designed as a seat shell part. It can also be seen that the fluid chamber unit 9, the plate element 11, and the cover element 12 are each designed to be plate-like and thus require a minimal amount of installation space in the height axis. The fluid chamber unit 9, the plate element 11, and the cover element 12 extend substantially in one plane along the length axis X and the width axis Y.

Figure 4A:
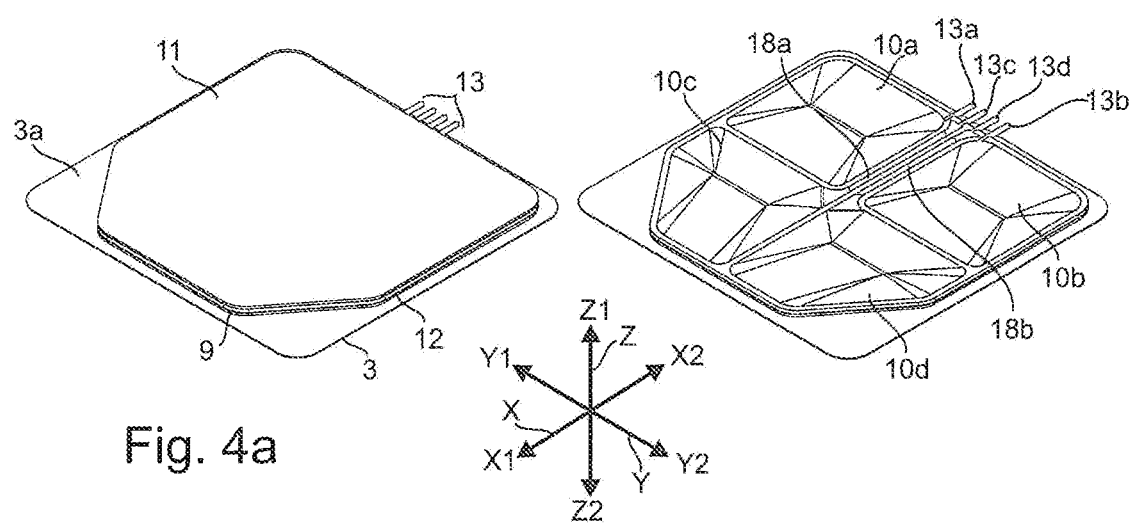
FIG. 4a, 4b are a detailed view of a fluid chamber unit with and without a plate element according to a preferred embodiment in a first state and in a second state.
Figure 4B:
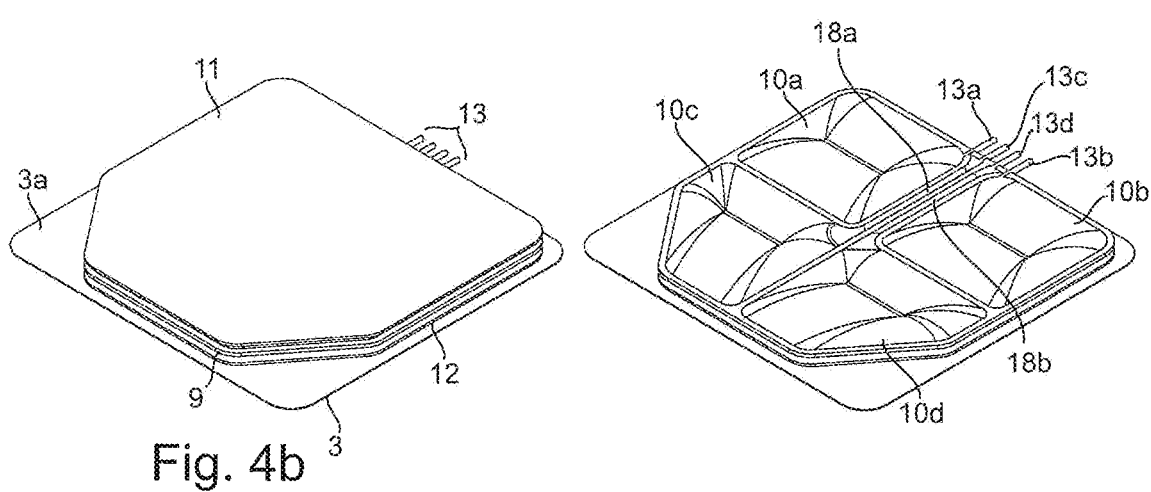

FIGS. 4a and 4b each show a seat plate part 3, on the upper side 3a of which a cover element 12 is arranged, a fluid chamber unit 9 being arranged thereabove in the height axis Z. In FIGS. 4a and 4b, a plate element 11 is arranged on the left side above the fluid chamber unit 9 in the height axis Z, the plate element 11 not being shown on the right side, and a clear view of the fluid chamber unit 9 from above being possible. Furthermore, in FIGS. 4a and 4b (on the left in each case), the cover element 12 and the plate element 11 are arranged substantially congruently, the cover element 12 and the plate element 11 being arranged so as to overlap in relation to the height axis Z of the vehicle seat 1, forming an intermediate second overlap region 16. The fluid chamber unit 9 is arranged completely within the second overlap region 16 between the cover element 12 and the plate element 11.

FIGS. 4a and 4b each show on the right that the fluid chamber unit 4 has a first fluid chamber 10a, a second fluid chamber 10b, a third fluid chamber 10c, and a fourth fluid chamber 10d. The first 10a and the second fluid chamber 10b are designed to be substantially square, the third 10c and the fourth fluid chamber 10d being designed to be substantially pentagonal. Each shape of the fluid chambers 10a-d can preferably be configured as desired and can be adapted to the given installation space of the vehicle seat 1 between the seat cushion part 4 and the seat plate part 3.

The first fluid chamber 10a and the second fluid chamber 10b are arranged adjacently along the width axis Y. The third fluid chamber 10c and the fourth fluid chamber 10d are also arranged adjacently along the width axis. Furthermore, the first fluid chamber 10a and the third fluid chamber 10c are arranged adjacently along the length axis X. The second fluid chamber 10b and the fourth fluid chamber 10d are in this case arranged adjacently along the length axis X. The third fluid chamber 10c and the fourth fluid chamber 10d are in this case arranged in front of X1 of the first fluid chamber 10a and the second fluid chamber 10b, as seen in the length axis.

Each of the fluid chambers 10a-d is individually fluidically connected to a fluid delivery device (not shown in this case), the connection being made in each case via a fluid connection element 13. The first fluid chamber 10a is fluidically connected via a first fluid connection element 13a, the second fluid chamber 10b is fluidically connected via a second fluid connection element 13b, the third fluid chamber 10c is fluidically connected via a third fluid connection element 13c, and the fourth fluid chamber 10d is fluidically connected via a fourth fluid connection element 13d to the fluid delivery device. In this way, a fluid can be introduced individually into each of the four fluid chambers 10a-d and can be removed individually from each of the four fluid chambers 10a-d.

The fluidic connection of the fluid chambers 10a-10d by means of the fluid connection elements takes place in relation to the length axis X at a rear end 17 of the fluid chamber unit 9, at which the first fluid chamber 10a and the second fluid chamber 10b are arranged, the rear end 17 being directed in the length axis X towards the rear X2. The fluid chamber unit 9 thus has a first fluid channel 18a and a second fluid channel 18b, the first fluid channel 18a fluidically connecting the third fluid chamber 10c to the third fluid connection element 13c and the second fluid channel 18b fluidically connecting the fourth fluid chamber 10d to the fourth fluid connection element 10d. The first 18a and the second fluid channel 18b run parallel to one another between the first 10a and the second fluid chamber 10b along the length axis X from the rear end 17 towards the front (direction X1).

FIG. 4a shows the fluid chamber unit 9 or each fluid chamber 10a-d in a first state, the fluid chamber unit 9 or the fluid chambers 10a-d having a first expansion in the height axis Z of the vehicle seat 1 in the first state. This first expansion represents a minimal expansion in the height axis and corresponds to a state that is substantially completely empty of fluid. FIG. 4b shows the fluid chamber unit 9 or each fluid chamber 10a-d in a second state, the fluid chamber unit 9 or the fluid chambers 10a-d having a second expansion in the height axis Z of the vehicle seat 1 in the second state. In this second state, a defined amount of fluid is introduced into each fluid chamber 10a-d. The second expansion in the height axis Z in the second state according to FIG. 4b is greater than the first expansion in the height axis Z in the first state according to FIG. 4a.

Figure 5A:
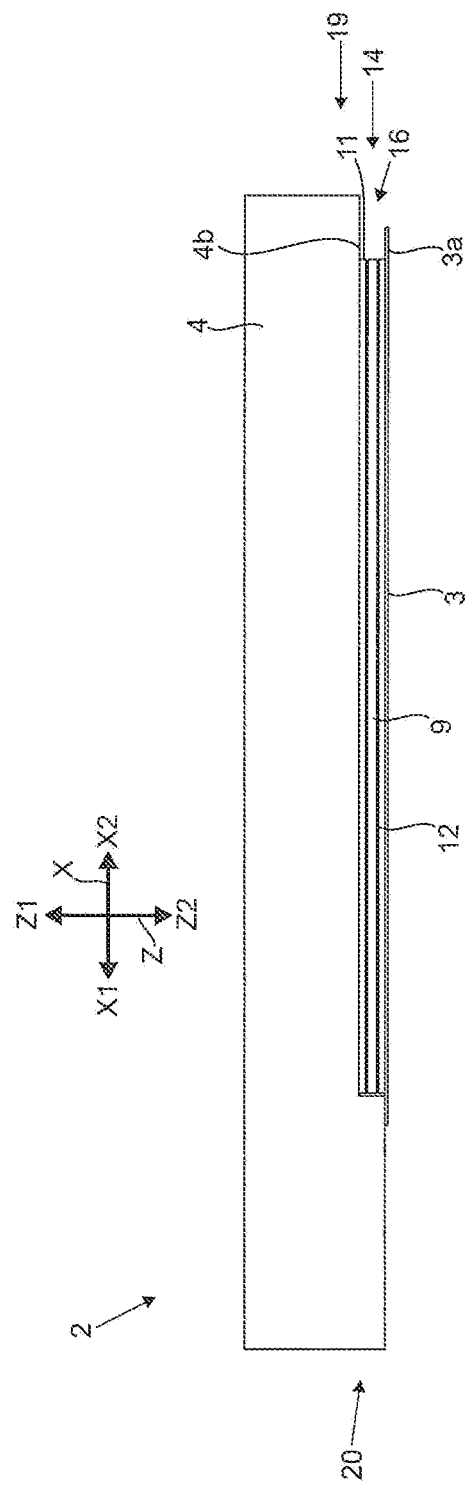
FIG. 5a, 5b is a cross-sectional view of an upper seat part according to a preferred embodiment in a first and a second state.
Figure 5B:
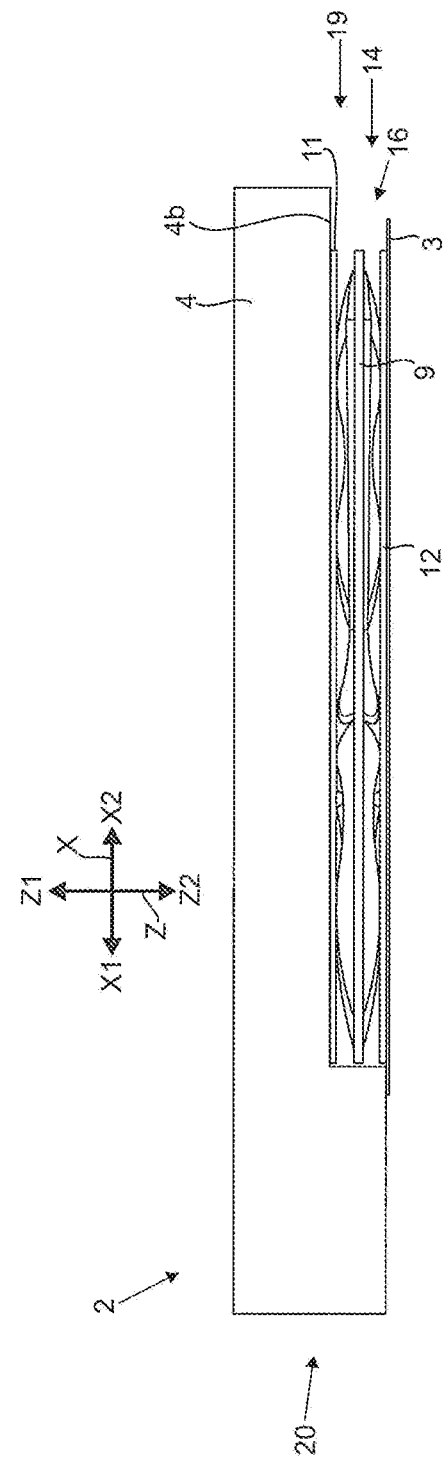

FIGS. 5a and 5b each show a cross-sectional view along the longitudinal axis X centred through a vehicle seat 1 in relation to the width axis Y of an upper seat part 2 with a seat plate part 3 and a seat cushion part 4 arranged above in the height axis Z. The upper seat part 2, as well as the seat cushion part 4 and the seat plate part 3, extend mainly in one plane along the length axis X and the width axis Y, an expansion in the height axis Z being smaller.

A cover element 12, a fluid chamber unit 9, and a plate element 11 are arranged within an overlap region 14, which is located between the seat plate part 3 and the seat cushion part 4 in relation to the height axis Z and is designed by the at least partially overlapping arrangement of the seat plate part 3 and the seat cushion part 4 in relation to the height axis Z. The cover element 12, the fluid chamber unit 9, and the plate element 11 are arranged completely within the first overlap region 14 between the seat plate part 3 and the seat cushion part 4.

The first overlap region is limited in relation to the height axis Z towards the top Z1 by the underside 4a of the seat cushion part 4 and towards the bottom Z2 by the upper side 3a of the seat plate part 3a. In the length axis X, the first overlap region 14 is delimited towards the front X1 by the seat cushion part 4. The seat cushion part 4 extends in the front portion 20 of the upper seat part 2 in relation to the height axis Z further towards the bottom Z2 than in the rear portion 19, the seat cushion part 4 ending flush (in contact) with the seat plate part 3 in the front portion towards the bottom Z2. In the rear portion 19, the first overlap region 16 is designed to be open, i.e., the seat cushion part 4 and the seat plate part 3 are designed to be non-contacting, whereby the fluid chamber unit 9 is advantageously easily accessible in order to be able to fluidically connect a fluid delivery device to the fluid chamber unit by means of fluid connection elements 13, for example.

The cover element 12 is arranged in the height axis Z above the seat plate part 3, to be in contact with the upper side 3a thereof, and is fastened thereto. Furthermore, the cover element 12 is connected to the seat plate part 3 by means of a force-fit, form-fit, or material-fit connection. The plate element 11, on the other hand, is arranged to be in contact in relation to the height axis Z below the seat cushion part 4, on the underside 4b thereof, the plate element 11 and the seat cushion part 4 being free of a connection. The cover element 12 and the plate element 11 are arranged so as to overlap completely in relation to the height axis Z, forming an intermediate second overlap region 16, the fluid chamber unit 9 being arranged completely within the second overlap region 16 between the cover element 12 and the plate element 11. The second overlap region 16 is arranged completely within the first overlap region 14. The fluid chamber unit 9 is fastened to the cover element 12, the plate element 11 and the fluid chamber unit 9 being free of connections.

FIG. 5a shows the fluid chamber unit 9 in a first state. In the first state, the fluid chamber unit 9 has a first expansion in the height axis Z. The first expansion in the height axis Z of the fluid chamber unit 9 corresponds to a minimum expansion of the fluid chamber unit 9 in the height axis Z. The fluid chamber unit 9 is in the first state when substantially all of the fluid has been completely removed.

FIG. 5b, on the other hand, shows the fluid chamber unit 9 in a second state and having a second expansion in the height axis Z. The second expansion of the fluid chamber unit 9 in the height axis Z occurs when fluid is introduced into the fluid chamber unit 9. The second expansion of the fluid chamber unit 9 is greater than the first expansion of the fluid chamber unit 9 in the height axis Z.

The expansion of the fluid chamber unit 9 (or the fluid chambers) takes place starting from the seat plate part 3 in the height axis Z towards the top Z1 in the direction of the seat cushion part 4. The expansion of the fluid chamber unit 9 in the height axis Z from the first state to the second state results in a reversible deformation of the seat cushion part 4, the movement/deflection of the fluid chamber unit 9 in the height axis Z being transmitted by means of the flexible plate element 11 in a planar manner to the seat cushion part 4. The movement/deflection is in turn transmitted from the seat cushion part 4 to a person sitting on the seat cushion part 4 or the vehicle seat 1.

Figure 6:
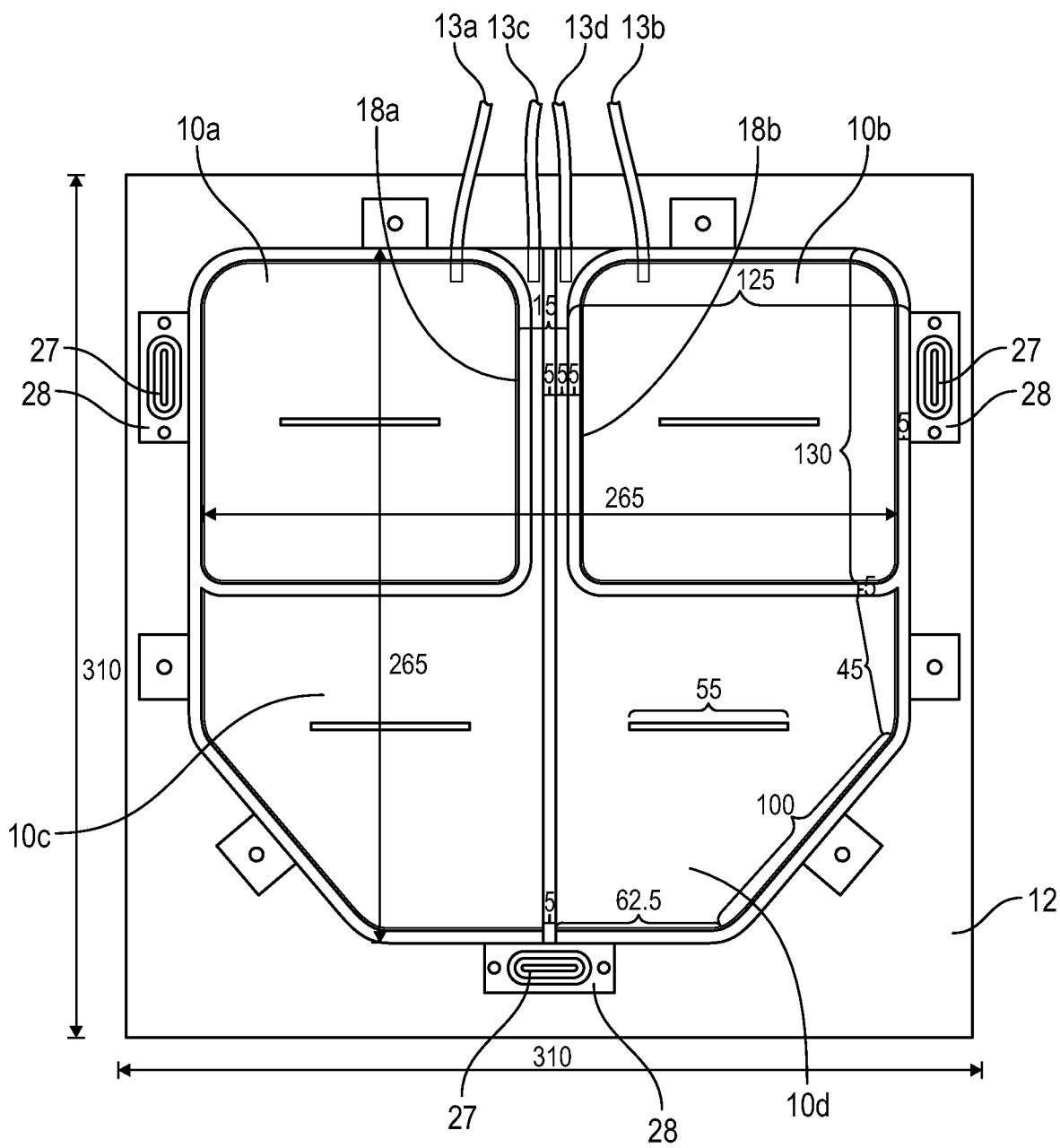
FIG. 6 is a plan view of a fluid chamber unit in an uninstalled state according to a preferred embodiment.

FIG. 6 shows a fluid chamber unit 9 having four fluid chambers 10a-d. The fluid chamber unit 9 is fastened by means of fastening elements 27 (three fastening elements in this embodiment) to the cover element 12 located below it in the height axis Z. The fastening elements 27 are preferably designed as clips. The fastening elements 27 fasten the fluid chamber unit 9 to the cover element 12 via fastening portions 28 of the fluid chamber unit 9, which are arranged circumferentially on the fluid chamber unit 9.

Figure 7:
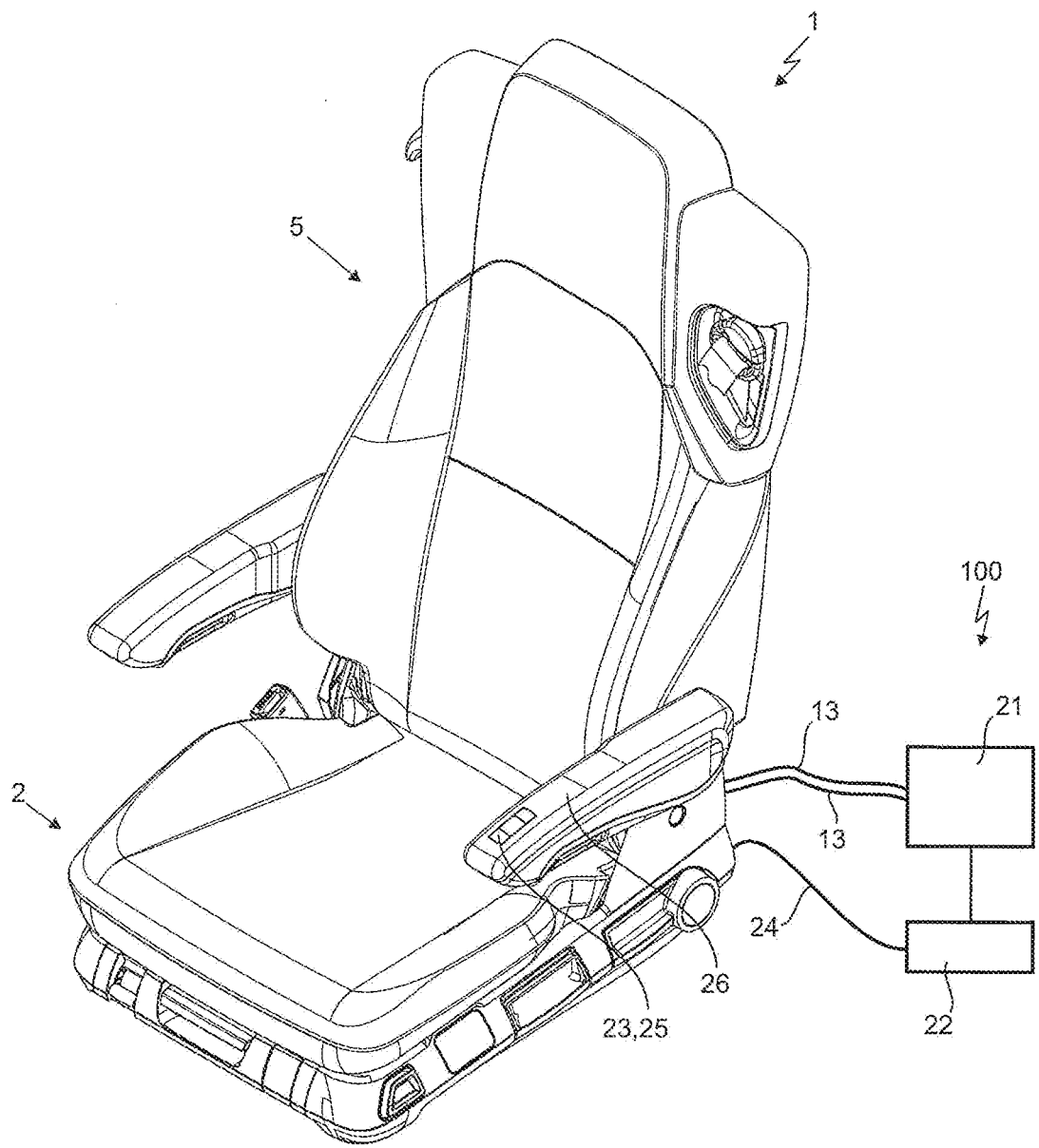
FIG. 7 is a schematic representation of a system according to a preferred embodiment.

FIG. 7 schematically shows one preferred embodiment of the system 100 according to the invention. The system 100 comprises the vehicle seat 1 according to the invention having a fluid delivery device 21 and a control unit 22, and an activation unit 25 having an operating unit 23.

The control unit 22 is connected at least for signalling purposes via a signalling connection 24 to the activation unit 25 or the operating unit 23 and is connected at least for signalling purposes, preferably power-electronically, to the fluid delivery device 21. The fluid delivery device 21 is connected to the fluid chamber unit 9 via at least two fluid connection elements 13 or is connected, in each case, independently of one another via a fluid connection element 13, to one of the at least two fluid chambers 10.

According to the embodiment shown, the activation unit 25 and the operating unit 23 are arranged together in an armrest 26 of the vehicle seat 1. In this position, the operating unit can be actuated manually in a particularly simple manner by a person sitting on the vehicle seat 1. The activation unit 25 is designed to transmit an activation signal via the signalling connection 24 to the control unit 22 when the operating unit 23 is actuated, whereupon the control unit outputs a pulse-width-modulated control signal to the fluid delivery device 21, and an introduction/removal of a fluid into at least one fluid chamber 10 of at least two fluid chambers 10 of a fluid chamber unit 9 takes place.

All features disclosed in the application documents are claimed as being substantial to the invention, provided that they are, individually or in combination, novel over the prior art.

LIST OF REFERENCE SIGNS

1 Vehicle seat
100 System
2 Upper seat part
3 Seat plate part
3a Upper side of the seat plate element
3b Underside of the seat plate element
4 Seat cushion part
4a Upper side of the seat cushion part
4b Underside of the seat cushion part
5 Backrest part
6 Back plate part
7 Back cushion part
8 Seat base part
9 Fluid chamber unit
10 Fluid chamber
10a, b, c, d Fluid chambers
11 Plate element
12 Cover element
13 Fluid connection element
13a, b, c, d Fluid connection elements
14 First overlap region
15 Region
16 Second overlap region
17 Rear end of the fluid chamber unit
18a, b Fluid channel
19 Rear portion
20 Front portion
21 Fluid delivery device
22 Control unit
23 Operating unit
24 Signalling connection
25 Activation unit
26 Armrest
27 Fastening elements
28 Fastening portions

What is claimed is:
1. A vehicle seat comprising:
an upper seat part for receiving a person, which upper seat part comprises a seat plate part and a seat cushion part, the seat cushion part being arranged above the seat plate part in relation to a height axis of the vehicle seat, and the seat plate part and the seat cushion part being arranged so as to at least partially overlap in relation to the height axis, forming an intermediate first overlap region, wherein a fluid chamber unit having at least two fluid chambers is arranged at least partially within the first overlap region between the seat plate part and the seat cushion part, a control unit being provided, designed to introduce and to remove a fluid into/from the at least two fluid chambers so that an expansion in the height axis of the at least two fluid chambers can be controlled, wherein the at least two fluid chambers are each designed to receive the fluid, and a fluid delivery device being provided, which is connected to the control unit at least for signalling purposes, which fluid delivery device is at least fluidically connected, independently, to each of the at least two fluid chambers, and being designed to transport the fluid into and/or from each of the at least two fluid chambers, it being possible for the fluid to be introduced individually into each of the at least two fluid chambers and to be removed individually from each of the at least two fluid chambers.

2. The vehicle seat according to claim 1, wherein the at least two fluid chambers are each designed to receive the fluid, and a fluid delivery device being provided, which is connected to the control unit at least for signalling purposes, which fluid delivery device is at least fluidically connected, independently, to each of the at least two fluid chambers, and being designed to transport the fluid into and/or from each of the at least two fluid chambers, it being possible for the fluid to be introduced individually into each of the at least two fluid chambers and to be removed individually from each of the at least two fluid chambers.

3. The vehicle seat according to claim 1, wherein the at least two fluid chambers are arranged adjacently in relation to a width axis or a length axis of the vehicle seat.

4. A vehicle seat, comprising:
an upper seat part for receiving a person, which upper seat part comprises a seat plate part and a seat cushion part, the seat cushion part being arranged above the seat plate part in relation to a height axis of the vehicle seat, and the seat plate part and the seat cushion part being arranged so as to at least partially overlap in relation to the height axis, forming an intermediate first overlap region,
wherein a fluid chamber unit having at least two fluid chambers is arranged at least partially within the first overlap region between the seat plate part and the seat cushion part, a control unit being provided, designed to introduce and to remove a fluid into/from the at least two fluid chambers so that an expansion in the height axis of the at least two fluid chambers can be controlled, and
wherein the fluid chamber unit is designed to be substantially plate-like, a cover element being arranged below the fluid chamber unit and between the seat plate part and the fluid chamber unit in relation to the height axis, and a plate element being arranged above the fluid chamber unit and between the seat cushion part and the fluid chamber unit in relation to the height axis, the fluid chamber unit being arranged between the cover element and the plate element in relation to the height axis.

5. The vehicle seat according to claim 4, wherein the cover element and the plate element are arranged so as to at least partially overlap in relation to the height axis, forming an intermediate second overlap region, the fluid chamber unit being at least partially arranged within the second overlap region between the cover element and the plate element, and the cover element and the plate element being arranged at least partially within the first overlap region between the seat plate part and the seat cushion part.

6. The vehicle seat according to claim 4, wherein the cover element is mechanically connected to the fluid chamber unit, the cover element consisting of a flexible material and the plate element being designed to be planar.

7. The vehicle seat according to claim 4, wherein the cover element and the plate element are arranged so as to at least partially overlap in relation to the height axis, forming an intermediate second overlap region, the fluid chamber unit being completely arranged within the second overlap region between the cover element and the plate element, and the cover element and the plate element being arranged completely within the first overlap region between the seat plate part and the seat cushion part.

8. The vehicle seat according to claim 4, wherein the cover element is mechanically connected to the fluid chamber unit, the cover element consisting of a textile material, and the plate element being designed to be planar and consisting of a flexible material.

9. The vehicle seat according to claim 4, wherein the cover element is mechanically connected to the fluid chamber unit, the cover element consisting of a textile material, and the plate element being designed to be planar and consisting of a plastics material.

10. A system, comprising:
vehicle seat, comprising:
an upper seat part for receiving a person, which upper seat part comprises a seat plate part and a seat cushion part, the seat cushion part being arranged above the seat plate part in relation to a height axis of the vehicle seat, and the seat plate part and the seat cushion part being arranged so as to at least partially overlap in relation to the height axis, forming an intermediate first overlap region;
wherein a fluid chamber unit having at least two fluid chambers is arranged at least partially within the first overlap region between the seat plate part and the seat cushion part, a control unit being provided, designed to introduce and to remove a fluid into/from the at least two fluid chambers so that an expansion in the height axis of the at least two fluid chambers can be controlled, and
an activation unit that is connected at least for signalling purposes to the control unit and which is designed to transmit an activation signal to the control unit to initiate an introduction and/or removal of a fluid into/from at least one fluid chamber of at least two fluid chambers of a fluid chamber unit.

11. The system according to claim 10, wherein the activation unit comprises a manually actuatable operating unit and/or a body function recognition unit, the body function recognition unit being designed to detect at least one body function of a person sitting on the vehicle seat, and having at least one first sensor.

12. A method for operating a system according to claim 10, comprising the steps of:
a) receiving an activation signal from an activation unit by means of a control unit;
b) outputting a pulse-width-modulated control signal to a fluid delivery unit by means of the control unit; and
c) introducing a fluid into at least one fluid chamber of at least two fluid chambers of a fluid chamber unit.

13. A vehicle, in particular a motor vehicle, comprising the system according to claim 10.

14. The system according to claim 10, wherein the system is arranged in a vehicle.

\* \* \* \* \*